United States Patent [19]

Erby et al.

[11] 3,954,807

[45] May 4, 1976

[54] CATALYTIC PRODUCTION OF POLYHALO-KETO-ALKENOIC ACIDS

[75] Inventors: William A. Erby, Alburtis; James F. Tompkins, Allentown, both of Pa.

[73] Assignee: Air Products and Chemicals, Inc., Allentown, Pa.

[22] Filed: Aug. 19, 1974

[21] Appl. No.: 498,800

Related U.S. Application Data

[60] Division of Ser. No. 292,384, Sept. 26, 1972, Pat. No. 3,842,126, which is a continuation of Ser. No. 723,283, April 22, 1968, abandoned.

[52] U.S. Cl............................ 260/343.6; 260/405.5; 260/408; 260/501.15; 260/501.16; 260/544 Y; 424/312; 424/318
[51] Int. Cl.²........................................ C07D 307/34
[58] Field of Search...................... 260/343.6, 539 R

[56] References Cited
UNITED STATES PATENTS 2,557,779    6/1951    Button et al.................. 260/539 R
3,862,220    1/1975    Erby et al....................... 260/539 R

*Primary Examiner*—Lorraine A. Weinberger
*Assistant Examiner*—Jane S. Myers
*Attorney, Agent, or Firm*—Leroy Whitaker; Everet F. Smith

[57] ABSTRACT

Halogenation of $C_5$ - $C_{10}$ saturated keto mono-carboxy acids or their acidogenic derivatives with elemental halogen in the presence of certain catalysts to yield olefinic halogenated compounds (e.g. acids and lactones) containing at least four halogen atoms per molecule is disclosed. The catalyst selected depends upon the particular end product desired. Halogenated products of the process are useful as insecticides, plant growth control agents and defoliants. Particularly useful products are those olefinic polychlorinated derivatives of 4-keto-pentanoic acid which contain at least four chlorine atoms per molecule such as, for example, 2,3,5,5,5-pentachloro-4-keto pentenoic acid.

3 Claims, No Drawings

CATALYTIC PRODUCTION OF POLYHALO-KETO-ALKENOIC ACIDS

This is a division of application Ser. No. 292,384 filed Sept. 26, 1972, now U.S. Pat. No. 3,842,126, which in turn is a continuation of application Ser. No. 723,283, filed Apr. 22, 1968, now abandoned.

BACKGROUND OF THE INVENTION

1. Field of the Invention

The present invention is concerned with novel methods for the catalytic synthesis of polyhalogenated and perhalogenated keto alkenoic acids, such as, for example, halogenated $C_5$ to $C_{10}$ mono-carboxylic acids; from the corresponding saturated keto acids their esters, amides, anhydrides, lactones, acyl halides, and other acidogenic derivatives. More particularly, it pertains to methods of catalytically chlorinating and/or brominating 4-keto-pentanoic acids and their derivatives to obtain acyclic and cyclic olefinic products which contain at least 4 halogen atoms per molecule.

2. Description of the Prior Art

While various investigators have reported the chlorination of 4-keto $C_4$ to $C_{10}$ acids to the mono or dichloro stage, there is no report to date of any direct combined chlorination and dehydrogenation of such acids (or their acidogenic derivatives) to the unsaturated polyhalogenated or perhalogenated stage. As used herein, the terms "polyhalogenated" and "polychlorinated" refer, respectively, to compounds containing at least four halogen atoms per molecule (which may be of the same or of different halogens) and to compounds which contain at least four chlorine atoms per molcule. The terms "perhalogenated" and "perchlorinated" refer, respectively, to compounds in which all of the hydrogen atoms attached to carbon atoms in the molecule are substituted with halogen atoms (which may be of the same or different halogens), and to compounds in which all of the hydrogen atoms attached to carbon atoms are substituted with chlorine atoms. The term "halogen" is intended to include chlorine, bromine or combinations thereof.

A common 4-keto-pentanoic acid, which is available in commerce, is levulinic acid. Early attempts to chlorinate levulinic acid directly resulted only in the production of mono-and dichloro derivatives. [Seissl, Annallen, 249, 288–303 (1888).] A number of polychloro-pentenoyl ketones, acids, acid halides and anhydrides have since been prepared by methods other than by the direct chlorination of levulinic acid [Zincke, Berichte der Deutsche Chemische Gessellschaft, 23, 240, (1890); 24, 916, (1891); 25, 2221, (1892); 26, 506, (1893); and 26, 317, (1893)].

U.S. Pat. No. 3,275,505 does disclose the direct halogenation of levulinic acid. However, the reaction temperatures are between 100° and 125° C and, even with high degrees of halogenation, no more than four atoms of halogen are added per molecule of levulinic acid. Further, there is no conversion of the acid from a saturated to an olefinic compound.

BRIEF SUMMARY OF THE INVENTION

Briefly summarized, the invention pertains to the catalytic halogenation, particularly with chlorine, of saturated 4-keto mono-carboxylic acids of which levulinic acid is a prime example. While the invention may be utilized in connection with either chlorine or bromine or both, those compounds produced from chlorine and/or bromine and levulinic acid are possessed of particular utility in connection with growth control of plants and in insecticidal applications. One particular compound, which can be made by processes of the invention, and which is designated 2,3,5,5,5,-pentachloro-4-keto pentenoic acid has a unique capacity for wilting the foliage of woody jungle plants such as cotton. This characteristic is the basis for a novel method of harvesting cotton which is described in co-pending application Ser. No. 632,937, now U.S. Pat. No. 3,472,004 entitled "Method of Harvesting Cotton". Further, chlorinated compounds of the invention are of value as jungle defoliants. Other uses of the compounds which may be made by the instant process are described in the co-pending application Ser. No. 541,096, now U.S. Pat. No. 3,557,546 entitled "Preparation and Use of Polychloro Keto-Alkenoic Acids".

In most general terms, the invention contemplates the catalytic chlorination and/or bromination of saturated 4-keto mono-carboxylic acids or their acidogenic derivatives (e.g. esters amides, etc.) with elemental halogen over relatively long periods of time and at elevated temperatures. Since the reactions are exothermic, it is usually preferred to halogenate at rates which prevent violent fluctuations of temperature such as would cause product degradation or undue increase in by-product formation. When batch processes are used, it is preferred to raise reaction temperatures gradually as the reaction proceeds over a period of time to the maximum limits.

Conditions utilized are always severe enough to cause both dehydrogenation and the addition of at least four halogen atoms per molecule of acid. Under more severe conditions, additional halogen may be incorporated to reach the perhalogenated state and, further, to cause formation of cyclic compounds.

The catalysts used in connection with the invention are limited to the cations iron, aluminum, zinc, titanium, cobalt, magnesium and calcium. while it is often most convenient to introduce the catalysts as salts, preferably chlorides, such salts need not be utilized as the source of the desired cation. In some instances the elemental metal may be utilized in the form of shavings or filings and the catalyst, in effect, formed in situ due to the reaction with halogen. Thus, when the term "cation" is used herein it is intended to encompass all sources of the cations and all means for introducing them into the reaction environment.

The amount of catalyst used, calculated as the chloride, and stated as weight per cent of the 4-keto monocarboxylic acid or acidogenic material may vary from 1-15% with a range of from 5–10% being generally preferred. In any event the catalytic amount necessary to optimize the reaction varies with reactants and reaction parameters but can, nonetheless, be readily determined by those skilled in the art.

The reactions can best be ilustrated with respect to the chlorination of levulinic acid and the summary discussion which follows is generally related to the examples in the discussion of the preferred embodiments below. These embodiments utilize levulinic acid or acidogenic derivatives thereof.

a. Iron Catalyst

Iron cation, preferably introduced as $FeCl_3$, has a unique effect on the reaction. Its use leads selectively to the production of 2,3,4,5,5,5-hexachloro-2-pentenoyl-4-lactone at temperatures as low as 155°C and reaction times as short as 8 hours. The lactone may be hydrolyzed, preferably in the presence of chlorine, to yield 2,3,5,5,5-pentachloro-4-keto-pentenoic acid. By-products of the chlorination reaction are dichloro maleic anhydride (which is removed during hydrolysis) and some penta chloro lactones (which are also converted to the pentenoic acid during hydrolysis).

b. Aluminum and Other Catalysts

Particular cations selected from the group consisting of aluminum, zinc, titanium, cobalt, magnesium and calcium which may be introduced, for example, respectively, as aluminum chloride, zinc chloride, titanium tetrachloride, cobaltic chloride, magnesium chloride and calcium chloride, cause the reaction to follow still another course. When these catalysts are used, a high yield of tetrachloro-4-keto-pentenoic acid (e.g. 3,5,5,5,-tetrachloro-4-keto pentenoic acid) is obtained by reacting levulinic acid with chlorine for about 3 hours at temperatures below 140°C. With the continuation of chlorination and the raising of the temperature above 150°C (preferably 155°C), there is quantitative conversion of the product to 2,3,5,5,5,-pentachloro-4-keto pentenoic acid after a period of about 20 to 30 hours. The purity of the product obtained in this manner is comparable to that obtained when the lactone produced in the ferric chloride catalyzed reaction is hydrolyzed.

The above reactions may be conducted with bromine instead of chlorine. Further, a reaction may be begun with one type of halogen, discontinued before perhalogenation is completed, and reacted with yet another halogen to the completion of halogenation so that a given molecule will contain atoms of different halogens.

The halogenated compounds produced by the novel method of the present invention from 5 carbon keto carboxy acids correspond, in form of the carboxylic acids or their esters, to the formula:

wherein $x$ is O or 1, and R is H or the residue of an esterifying organic hydroxy compound, such as an alcohol or phenol.

Compounds corresponding to the above formula are produced in high yields and exceptional purity in accordance with the invention by the catalytic chlorination of levulinic acid or its acidogenic derivatives under controlled conditions of time and temperature to obtain an olefinic linkage at the carbon in the position alpha to the carboxy group. Illustrative of the compounds thus obtained and certain derivatives (e.g. esters and salts therof) are:

1) 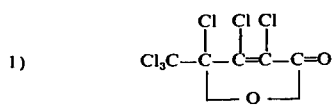

2,3,4,5,5,5-hexachloro-2-pentenoyl-4-lactone (perchloro angelica lactone)

2) 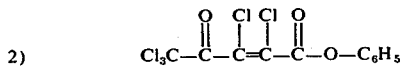

phenyl-2,3,5,5,5-pentachloro-4-keto-2-pentenoate

3) 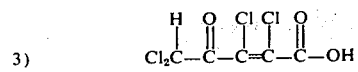

2,3,5,5,-tetrachloro-4-keto-2-pentenoic acid

4) 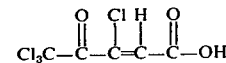

3,5,5,5,-tetrachloro-4-keto-2-pentenoic acid

5) 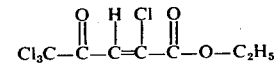

ethyl 2,5,5,5-tetrachloro-4-keto-2-pentenoate

6) 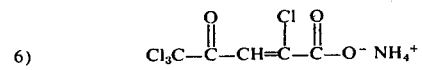

ammonium salt of 2,5,5,5-tetrachloro-4-keto-2-pentenoic acid

7) 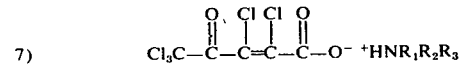

wherein $R_1$ is alkyl and $R_2$ and $R_3$ are each alkyl or hydrogen, these compounds being amine salts of 2,3,5,5,5-pentachloro-4-keto-2-pentenoic acid.

The polychloro-compounds so produced have been found to have pronounced activity as insecticides, herbicides and cotton defoliants, such that, in a process based upon low cost levulinic acid and chlorine, commercially valuable biologically active chemicals can be produced at low cost.

Esterification of the free acid can be effected with monohydric or polyhydric alcohol. Thus, by reacting compound (1) with pentaerythritol, a mixture comprising mono-and di-esters may be obtained.

Ammonium and amine salts of the free acids can also be formed by reacting the same, respectively, with ammonia or primary, secondary or tertiary alkyl amines including, for example, dipropyl amine, isopropyl amine, N,N-dimethyl hexadecylamine, N-N-dimethyl octadecylamine, N-N-dimethyl dodecylamine and cocoamine.

Accordingly, it is an object of the invention to provide a method whereby catalytic halogenation of $C_5$ to $C_{10}$ saturated keto mono carboxy acids or their acidogenic derivatives at temperatures below 210°C effects both halogenation and dehydrogenation.

It is a further object of the invention to provide a direct method of halogenation where, selectively, dependent upon the catalyst and reaction conditions utilized, as well as the reactants present, one may obtain acyclic halogenated olefinic keto acids or related cyclic compounds both of which are capable of further reactions such as esterification.

It is additionally an object of the invention to provide processes for the catalytic halogenation of keto carboxy acids, using catalysts which selectively yield predetermined end-products, under predictable reaction conditions and times.

These and other objects of the invention will be apparent to those skilled in the art from a consideration of the exemplary description which follows.

It should be appreciated that neither the abstract of the disclosure nor the summary of the invention above is intended to constitute a limitation on its extent. They are inserted merely as aids in information retrieval and, therefore, the true scope of the invention is to be determined only by a reasonable interpretation of the appended claims in light of the disclosure herein contained

DESCRIPTION OF PREFERRED EMBODIMENTS

The desired compounds are produced, in accordance with the invention, for example, by passing chlorine into levulinic acid or into an acidogenic derivative of levulinic acid over an extended period of time while raising the temperature gradually from ambient temperature to an ultimate temperature which may be as high as 210°C, depending upon the catalyst used. As halogen is added, the activation energy for subsequent substitutions increases. Therefore, it is necessary to increase the temperature as the reaction proceeds. In equivalent continuous processes, cold feed can be added to large agitated bodies of liquid maintained at optimum temperature and such fresh feed is, in effect, gradually raised in temperature.

Premature elevation of temperature can induce decomposition and polymerization of unsuitable intermediates. However, the thermal stability of the intermediates increases as the halogen content increases, which allows the reaction temperature to be safely increased as halogenation proceeds. Since the reactions are exothermic, once they have been initiated, it is important to control the rate of addition of halogen so that temperatures will not rise above the capacity for thermal stability of the system in its then current degree of halogenation. Briefly, then, the rate of addition of halogen is a function of temperature in practicing the invention.

There are thus obtained in high yield and good purity, polychloro and perchloro keto- pentenoic acids and their derivatives, having four or more chlorine atoms per molecule. The acids obtained can be readily converted to the corresponding salts, esters and amides by methods generally known in the art.

The distinct properties of the compounds obtained by the practice of the invention which render them useful, and effective as insecticidal and herbicidal compositions, are believed to reside in the simultaneous presence in the carboxylic compound of the polychloro function combined with the effect of the olefinic linkage, and the keto type structure. Despite the high insecticidal activity displayed by these compounds, they are highly selective in their action on plants, whereby they also have utility as plant growth control and defoilating agents.

The following examples illustrate some embodiments of the invention but are not intended to limit the same. The special results obtained by the use of the iron cation should be particularly noted.

EXAMPLE 1

One hundred sixteen grams of levulinic acid were placed in a reactor equipped with a gas dispersion tube, a stirrer and a heating-cooling mechanism. Ferric chloride hexahydrate (1.35 gm.) was added to the levulinic acid. Chlorine was then passed through the dispersion tube into the rapidly stirring mixture. An exothermic reaction occurred, and the temperature was allowed to increase to 100°C. It was maintained at this temperature by adjustment of the cooling mechanism. The reaction was allowed to continue until a decrease in the reaction exotherm was indicated by a drop in the temperature inside the reactor.

On completion of this phase of the reaction, the temperature was slowly raised to 125° to 130° by increasing the temperature of the mechanism. Care was taken during this operation to prevent darkening of the reaction mixture such as might be caused by raising the temperature too rapidly. Again an exotherm was noted. The chlorine flow rate during the rest of the reaction was maintained fast enough to insure that a small amount of chlorine was present in the reactor exit gas. The reactor was held at this temperature until the heat output of the reaction again decreased.

Upon completion of the second phase, the temperature was again raised to 155°C. The reaction was then maintained at 155°C until completion. Completion of the reaction was confirmed by infrared analysis of the sample. The sample spectrum contained no absorption peak between 2.5 and 3.5 microns. A very sharp carbonyl absorption band of high intensity appeared at 5.45 microns. This was accompanied by a small shoulder at 5.55 microns. An unsaturation absorption band was also evident at 6.15 microns.

The product was thus identified as comprising predominantly 2,3,4,5,5,5 hexachloro-2-pentenoyl-4-lactone. (i.e. perchloro-angelica lactone) having the following formula:

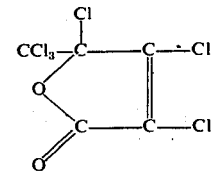

| | Found | Theory |
|---|---|---|
| Boiling Point | 74.5°C/0.2 mm Hg | |
| Refractive Index, 20°/D | 1.5465 | |
| Density, g/ml at 20°C. | 1.6357 | |
| Chlorine Content | 70.2% | 69.8% |
| Carbon Content | 20.2% | 19.8% |
| Molecular Weight | 315 | 305 |

Strong characterizing adsorption peaks for infra-red were at 1835 cm$^{-1}$ and 974 cm$^{-1}$. Weight recovery on the basis of this structure was 94% of theoretical.

Halogenated angelica lactone behaves, in its chemical reactions, as if it were an acyl halide of the type:

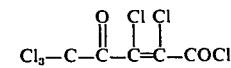

Thus, it was readily esterified by reaction with sodium phenoxide to yield the phenyl ester of pentachloro-4-keto-2-pentenoic acid.

EXAMPLE 2

Hydrolytic conversion of the product of Example 1 to 2,3,5,5,5-pentachloro-4-keto pentenoic acid was effected as follows:

The reaction product of Example 1 prior to hydrolysis consists primarily of the lactone and some of said pentenoic acid. Conversion of the lactone to the pentenoic acid was carried out by reducing the temperature of the product below 100°C and adding water (in an amount equal to 30% of levulinic acid used). This reaction mixture was then rapidly stirred, while a slow stream of chlorine was passed through the system with the temperature maintained at about 100°C.

When this hydrolysis was complete, the carbonyl region of the infrared spectrum of the product showed two bands, one at 5.5 and one at 5.6 microns. A broad acid-OH absorption band appeared at 3 microns thus indicating substantially complete conversion to said pentachloro-4-keto pentenoic acid.

The temperature was then allowed to drop to approximately 90° and enough water was added to cause phase separation. The water, in the upper layer, was then siphoned out of the reactor as completely as possible. The product was washed two more times with water and dried. It was, thereafter, identified as 2,3,5,5,5-pentachloro-4-keto pentenoic acid.

The following examples are illustrative of those embodiments of the invention using cations selected from the group consisting of aluminum, zinc, titanium, cobaltic, magnesium and calcium.

EXAMPLE 3

Levulinic acid (116 gm.) was placed in a reactor equipped with a gas dispersion tube, a stirrer and a heating-cooling mechanism. Anhydrous aluminum chloride (0.6 gm.) was added to the levulinic acid. Chlorine was then passed through the dispersion tube into the rapidly stirring mixture. An exothermic reaction occurred and the temperature was allowed to increase to 180°C. It was maintained at this temperature until the infra-red spectra indicated that complete conversion to 2,3,5,5,5-pentachloro-4-keto pentenoic acid had occurred.

Additional runs were made, using the same techniques, to determine the effective amount of $AlCl_3$ catalyst and it was thus determined that effective catalyst concentration can vary from 0.1 to 10%. Other runs were made to prove the effectiveness of the above-named specific cations in the reaction.

EXAMPLE 4

Levulinic acid (116 gm.) was placed in a reactor equipped with a gas dispersion tube, a stirrer and heating-cooling mechanism. Anhydrous aluminum chloride (5.3 gm) was added to levulinic acid. Chlorine was then passed through the dispersion tube into a rapidly stirring mixture. An exothermic reaction occurred and the temperature was allowed to increase to 150°C. It was maintained at this temperature until the infra-red spectra indicated that complete conversion to 2,3,5,5,5-pentachloro-4-keto pentenoic acid had occurred.

In reactions conducted in this manner yields of said pentachloro-4-keto pentenoic acid on the order 90% are common. Some 3.5% of tetrachloro acid results, with the balance of the product being lost by entrainment in the exit gas.

As indicated above, it is possible to control the reaction to selectively obtain a tetrachloro acid such as, for example, 3,5,5,5-tetrachloro-4-keto pentenoic acid. This is illustrated by the following example.

EXAMPLE 5

To an apparatus equipped with a stirrer, a condenser, and a gas dispersion apparatus were added levulinic acid and anhydrous aluminum chloride (0.5% of the weight of levulinic acid). The levulinic acid contained somewhere in the neighborhood of 0.5% water.

The reaction is started by passing chlorine through the system at the lowest temperature where levulinic acid is a liquid. An exothermic reaction occurs which causes the temperature to rise to approximately 100°C. The reaction mixture is kept at this temperature until the exotherm ceases, which is noted by a decrease in the temperature of the reactor. This is accompanied by a decrease in chlorine adsorption by the reaction mixture. When these phenomena are noted, the temperature can then be increased to 155°C and held at this temperature until the decrease in the reaction isotherm is again manifest by a temperature drop. At this point the reaction mixture contained substantially 100% 3,5,5,5-tetrachloro-4-keto-pentenoic acid as determined by sampling and analysis. Total reaction time was 12 hours to this point.

The temperature was then raised to approximately 180°C and held at this temperature, maintaining the reaction system saturated with chlorine, until total conversion to 2,3,5,5,5-pentachloro-4-keto-pentenoic acid occurred.

Other examples of similar reactions utilizing chlorine, bromine or both in succession as well as a variety of catalysts and starting materials are presented below in tabular form. The manipulative techniques used were generally similar to those described in Example 1.

| Example No. | Starting Acid | Halogen | Catalyst | Max. Temp. | Total Time (Hours) | Product |
|---|---|---|---|---|---|---|
| 6 | Levulinic acid | $Cl_2$ | $FeCl_3$ | 175°C | 8 | 2,3,4,5,5,5-hexachloro-4-pentenoyl lactone |
| 7 | Levulinic acid | $Cl_2$ | $ZnCl_2$ | 180°C | 30 | 2,3,5,5,5-pentachloro-4-ketopentenoic acid |
| 8 | Levulinic acid | $Cl_2$ | $TiCl_4$ | 180°C | 35 | 2,3,5,5,5-pentachloro-4-keto pentenoic acid |
| 9 | Levulinic acid | $Cl_2$ | $CoCl_3$ | 180°C | 40 | 2,3,5,5,5-pentachloro-4-keto pentenoic acid |
| 10 | Levulinic acid | $Cl_2$ | $MgCl_2$ | 180°C | 30 | 2,3,5,5,5-pentachloro-4-keto pentenoic acid |
| 11 | Levulinic acid | $Cl_2$ | $CoCl_2$ | 180°C | 30 | 2,3,5,5,5-pentachloro-4-keto pentenoic acid |
| 12 | 4-keto hexanoic acid | $Cl_2$ | $ZnCl_2$ | 200°C | 30 | 2,3,5,5,6-pentachloro hexenoic acid |
| 13 | Levulinic acid | $Br_2$ then $Cl_2$ | Al | 170°C | 16 | 2,5,5 trichloro-3,5-dibromo-4-keto pentenoic acid |
| 14 | 6,6-dimethyl-4-keto heptanoic acid | $Cl_2$ | $AlCl_3$ | 200°C | 30 | 2,3,5,5,6-pentachloro-6,6-dimethyl-4-keto heptenoic acid |

-continued

| Example No. | Starting Acid | Halogen | Catalyst | Max. Temp. | Total Time (Hours) | Product |
|---|---|---|---|---|---|---|
| 15 | 4-ketohexanoic acid | $Cl_2$ | $MgCl_2$ | 200°C | 30 | 2,3,5,5,6-pentachloro-4-ketohexenoic acid |
| 16 | 4-ketohexanoic acid | $Cl_2$ | $MgCl_2/AlCl_3$ | 200°C | 30 | 2,3,5,5,6-pentachloro-4-ketohexenoic acid |
| 17 | 4-ketohexanoic acid | $Br_2$ | $AlBr_3$ | 200°C | 30 | 2,3,5,5,6-pentabromo-4-ketohexenoic acid |
| 18 | Levulinic acid | $Br_2$ | $AlBr_3$ | 180°C | 30 | 2,3,5,5,5-pentabromo-4-ketopentenoic acid |
| 19 | Levulinic acid | $Br_2$ | Al | 180°C | 30 | 2,3,5,5,5-pentabromo-4-ketopentenoic acid |
| 20 | Levulinic acid | $Cl_2$ | Al | 180°C | 30 | 2,3,5,5,5-pentachloro-4-ketopentenoic acid |
| 21 | Levulinic acid | $Cl_2$ | Mg | 180°C | 30 | 2,3,5,5,5-pentachloro-4-ketopentenoic acid |
| 22 | 4-ketohexanoic acid | $Cl_2$ | Mg | 180°C | 30 | 2,3,5,5,6-pentachloro-4-ketohexenoic acid |
| 23 | Levulinic acid | $Cl_2$ | $MgCl_2$ | 160°C | 12 | 2,3,5,5,5-pentachloro-4-ketopentenoic acid |

Direct chlorination of levulinic acid readily forms the simple chloro derivative. The reaction has been shown by others to proceed with increasing difficulty only to the tetrachloro stage.

Surprisingly, we have found that on extended chlorination, in the presence of selected catalysts, at temperatures no higher than 210°C, and preferably in the range of 170°–200°C, and in the presence of excess chlorine it is possible to go beyond this point. Using methods of the invention, it is possible to substitute chlorine for four or more hydrogen atoms and to simultaneously split off two hydrogen atoms (as HCl) to produce a new species of olefinically unsaturated derivatives. The catalysts operable in the invention are specific and total broad generally recognized classes (e.g. Lewis Acid Catalysts) are unsuitable. Further, iron as a catalyst results in the production of specific types of compounds (i.e. lactones) and is atypical of even the unique group of operable catalysts disclosed herein.

The products of halogenation, according to the invention, are mono-olefinically unsaturated at the tetra-, penta- and hexahalo levels. Use of the catalysts specified allows the reactions to proceed fully at temperatures below 210°C and in relatively short times. Further, choice of catalyst favors the production of predetermined types of derivatives.

The reaction rate, up to a certain point, is a function, inter alia, of the amount of catalyst present. Since water can partially and temporarily decrease catalyst activity it is preferred to utilize anhydrous reactants and anhydrous catalysts. However, when some water is present, the initial reaction period is utilized for ridding the system of water.

Throughout the reaction, temperature should be carefully controlled so that the reaction exotherm does not exceed the desired limit. Otherwise, particularly during the early stages of halogenation, one obtains only polymeric products of a tarry nature.

The process of producing unsaturated polychloro-4-keto pentenoic acid or its acidogenic derivatives, containing at least four chlorine atoms per molecule, has been exemplified above starting with levulinic acid. However, the process is not limited to this starting material. Esters, acyl halides, anhydrides and lactones of levulinic acid can be used. Further, the monochloro and dichloro derivatives of levulinic acid, known in the prior art, can be used whether the chlorine is in the alkyl chain, in the acyl group or in both. Homologous keto acids and keto acids relatable to levulinic acid are similarly polychlorinatable or perchlorinatable in accordance with the invention provided they contain the structure:

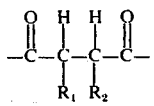

wherein $R_1$ and $R_2$ are independently selected from the group consisting of hydrogen, halogen and lower alkyl.

Temperature limits have been given for the halogenation reactions. However, it will be appreciated by those conversant with the art that reasonable variations can be made in the temperature and time of halogenation by means of which the rate and extent of halogenation and dehydrogenation can be varied. For instance, while chlorination and dehydrogenation of levulinic acid can be achieved in 30 hours with reaction temperatures on the order of 180°C, one can by having a significant portion of reaction time in the range of 190° to 210°C achieve a similar degree of chlorination and dehydrogenation in a somewhat shorter time, though with some loss of selectivity. Utilizing the route where iron is used as a catalyst, followed by hydrolysis to the free acid, the loss of selectivity becomes irrelevant.

After the halogenation reaction described above, the reaction products may be further reacted to produce esters, amides and salts. When salts are desired of those products which are lactones, it is first necessary to obtain them in their free acid form by hydrolysis. The following are illustrative examples of salt formation:

EXAMPLE S-1

The product of Example 3 was dissolved in ether (other suitable solvents include, for example, toluene) and ammonia was slowly bubbled through the solution. An excess of acid was maintained in the media in order to increase yield. The ammonium salt of 2,3,5,5,5-pentachloro-4-keto-2-pentenoic acid was obtained. A portion of the product was further purified by recrystallization from ethyl acetate.

EXAMPLE S-2

The product of Example 2, subsequent to the hydrolysis step, was subjcted to the method of Example S-1 and the same ammonium salt was obtained as from Example S-1.

Salts of the various halogenated keto acids of the invention are obtained by reacting them (in their acid form) with ammonia or organic amines, preferably those containing from 1 to 18 carbons. As used henceforth herein, the term "organic amines" is intended to encompass such compounds as well as amines which have been reacted with an alkylene oxide. Amines which have been utilized in this connection include, for example, n-octylamine, N-oleyl-1,3-propylene diamine, ethylamine, diethyl amine, triethylamine, propylamine, dipropyl amine, isopropyl amine, ethanol amine, diisopropyl amine, butyl amine, dibutyl amine, hexyl amine, 2-Ethylhexyl amine, N-methylbutyl amine, etc.

One of the utilities of the compounds of the process is exemplified by data obtained using the product of Example 1 as the active ingredient. Herbicidal characteristics were determined by spraying the active material at a rate of 2 lb./acre using a water suspendable oil formulation thereof. In the table results are reported on a linear numerical scale where 0 indicates no effect and 10 indicates a complete kill A. Weeds

| | |
|---|---|
| Pigweed | 10 |
| Johnsongrass | 9 |
| Setaria | 8 |

B. Crops

| | |
|---|---|
| Corn | 6 |
| Oats | 2 |
| Wheat | 1 |

Another utility possessed by commpounds which can be made using the processes of the instant invention arises in connection with the wilt-harvesting of cotton. Application of these materials to cotton prior to harvesting causes wilting of foliage to occur in a short time and promotes boll opening. By harvesting cotton when the plant is wilted, yield and quality of cotton are improved. Further, thereafter, defoliation occurs and the balance of the cotton can be harvested. All of these agricultural techniques are discussed at length in co-pending application Ser. No. 632,937 referred to above. Suffice it to say at this point, that it is commercially desirable for the compounds under consideration to wilt and/or defoliate cotton plants. Some test data demonstrative of this ability is given below in a series of tests performed with the compound of Example 3 and various of its salts. Applications of the indicated compound at the rate of active ingredient shown was in the form of a water extendible concentrate which was diluted to a spray volume equivalent to 20 gallons per acre.

| Compound of | | Rate (lb./acre) | % Wilt 24 hrs. | 48 hrs. | % Defoliation 5 days | 13 days |
|---|---|---|---|---|---|---|
| 1 | Example 3 | 4 | 80 | 80 | 50 | 50 |
| 2 | Ammonium salt | 4 | 80 | 90 | 95 | 95 |
| 3 | Monomethyl amine salt | 4 | 40 | 40 | 25 | 35 |
| 4 | Monethyl amine salt | 4 | 50 | 55 | 30 | 30 |
| 5 | Monoisopropyl amine salt | 4 | 55 | 70 | 20 | 20 |
| 6 | Triethylamine salt | 4 | 40 | 50 | 5 | 5 |
| 7 | Monoethanolamine salt | 4 | 40 | 40 | 25 | 25 |
| 8 | Triethanolamine salt | 4 | 20 | 20 | 2 | 2 |

It has thus been demonstrated how methods of the invention achieve the objects initially stated and produce compounds having various agricultural utility.

Obviously, many modifications and variations of the invention, as hereinbefore set forth, may be made without departing from the spirit and scope thereof. Therefore, only such limitations should be imposed as are indicated in the appended claims.

We claim:

1. A method of producing 2,3,4,5,5,5-hexachloro-2-pentenoyl-4-lactone comprising: reacting chlorine gas with levulinic acid at liquid reactant temperatures between 155°C. and 210°C. in the presence of a catalytic amount of iron cation, said chlorine gas being introduced at a rate such that the heat of reaction will not cause the reaction temperature to exceed said limit, thereby effecting both addition of chlorine to and partial dehydrogenation of said acid molecule.

2. The method of claim 1 wherein said catalyst is introduced as $FeCl_3$.

3. The method of claim 1 wherein said catalyst is formed in situ from metallic iron.

* * * * *

UNITED STATES PATENT AND TRADEMARK OFFICE
CERTIFICATE OF CORRECTION

PATENT NO. : 3,954,807
DATED : May 4, 1976
INVENTOR(S) : William A. Erby, et al.

It is certified that error appears in the above-identified patent and that said Letters Patent are hereby corrected as shown below:

Column 2, line 39, "while" should read "While".

Column 2, line 44, "in situ" should read " "in situ" ".

Column 2, line 52, "1-15%" should read ".1-15%".

Column 2, line 57, "ilustrated" should read "illustrated".

Column 5, line 44, "readly" should read "readily".

Column 5, line 56, "defoilating" should read "defoliating".

Column 11, line 46, "commpounds" should read "compounds".

Signed and Sealed this

Fourteenth Day of December 1976

[SEAL]

Attest:

RUTH C. MASON
Attesting Officer

C. MARSHALL DANN
Commissioner of Patents and Trademarks